US012714663B2

(12) United States Patent
Iida et al.

(10) Patent No.: US 12,714,663 B2
(45) Date of Patent: Aug. 25, 2026

(54) COMPOSITION FOR SKIN EXTERNAL APPLICATION

(71) Applicant: KAO CORPORATION, Tokyo (JP)

(72) Inventors: Masayuki Iida, Odawara (JP); Ayumi Shimpo; Yukihiro Miyazaki, Odawara (JP)

(73) Assignee: KAO CORPORATION, Tokyo (JP)

( * ) Notice: Subject to any disclaimer, the term of this patent is extended or adjusted under 35 U.S.C. 154(b) by 760 days.

(21) Appl. No.: 17/789,363

(22) PCT Filed: Dec. 17, 2020

(86) PCT No.: PCT/JP2020/047244
§ 371 (c)(1),
(2) Date: Jun. 27, 2022

(87) PCT Pub. No.: WO2021/132033
PCT Pub. Date: Jul. 1, 2021

(65) Prior Publication Data

US 2023/0064727 A1 Mar. 2, 2023

(30) Foreign Application Priority Data

Dec. 27, 2019 (JP) ................................ 2019-238768

(51) Int. Cl.
*A61K 8/891* (2006.01)
*A61K 8/25* (2006.01)
*A61K 8/58* (2006.01)
*A61Q 19/08* (2006.01)

(52) U.S. Cl.
CPC ................ *A61K 8/891* (2013.01); *A61K 8/25* (2013.01); *A61K 8/585* (2013.01); *A61Q 19/08* (2013.01)

(58) Field of Classification Search
CPC ...................................................... A61K 8/891
See application file for complete search history.

(56) References Cited

U.S. PATENT DOCUMENTS

| | | | | |
|---|---|---|---|---|
| 2011/0117041 | A1 | 5/2011 | Chantal et al. | |
| 2011/0301247 | A1* | 12/2011 | Hayakawa | A61Q 17/04 528/33 |
| 2012/0269875 | A1 | 10/2012 | Tamura et al. | |
| 2019/0365632 | A1* | 12/2019 | Iyoku | A61Q 19/007 |
| 2021/0196586 | A1* | 7/2021 | Farran | A61K 8/26 |

FOREIGN PATENT DOCUMENTS

| | | | |
|---|---|---|---|
| CN | 103608384 | A | 2/2014 |
| CN | 104411285 | A | 3/2015 |
| CN | 105005104 | A | 10/2015 |
| EP | 2 444 062 | A2 | 4/2012 |
| EP | 2 492 301 | A1 | 8/2012 |
| EP | 4 129 410 | A1 | 2/2023 |
| EP | 4 129 417 | A1 | 2/2023 |
| FR | 2 659 551 | A1 | 9/1991 |
| JP | 2004-26731 | A | 1/2004 |
| JP | 2006-56861 | A | 3/2006 |
| JP | 2008-189609 | A | 8/2008 |
| JP | 2009-57308 | A | 3/2009 |
| JP | 2010-229094 | A | 10/2010 |
| JP | 2011-16734 | A | 1/2011 |
| JP | 2012-17317 | A | 1/2012 |
| JP | 2012-246446 | A | 12/2012 |
| JP | 2013-103885 | A | 5/2013 |
| JP | 2013-525452 | A | 6/2013 |
| JP | 2014-129261 | A | 7/2014 |
| WO | WO 2009/093534 | A1 | 7/2009 |
| WO | WO 2011/049248 | A1 | 4/2011 |
| WO | WO 2016/158011 | A1 | 10/2016 |
| WO | WO2019/044590 | A1 | 3/2019 |

OTHER PUBLICATIONS

Shin-Etsu, New Film Former, 2013, Shin-Etsu Chemical Co. Ltd., 1 (Year: 2013).*

"Dow Corning® FA 4002 ID Silicone Acrylate", Dow Corning Corporation, Mar. 25, 2009, Ref. No. 27-1226A-01, 4 pages URL: https://www.cossma.com/fileadmin/all/cossma/Archiv/ProductInfo/CS1709_16DowSiliAcry1.pdf.

Wikipedia: Decamethylcyclopentasiloxane, URL: https://en.wikipedia.org/wiki/Decamethylcyclopentasiloxane, 5 pages.

W. Dekant, et al., "Toxicology of decamethylcyclopentasiloxane (D5)", Regulatory Toxicology and Pharmacology 74 (2016) S67-S76.

Michael S. McLachlan, et al., "Concentrations and Fate of Decamethylcyclopentasiloxane (D5) in the Atmosphere", Environ. Sci. Technol. 2010, 44, 14, 5365-5370.

SCCS/1549/15, Final version of Jul. 29, 2016, Scientific Committee on Consumer Safety, SCCS, Opinion on decamethylcyclopentasiloxane (cyclopentasiloxane, D5) in cosmetic products, 78 pages.

Yin D., et al., "Progress in field of research work with respect to organosilicon gel used in cosmetics", China Surfactant Detergent & Cosmetics, vol. 43, No. 4, Aug. 2013, pp. 309-312 (with English abstract of p. 309).

(Continued)

*Primary Examiner* — Jessica Worsham

(74) *Attorney, Agent, or Firm* — Oblon, McClelland, Maier & Neustadt, L.L.P.

(57) ABSTRACT

A composition for external preparation for skin includes (A) from 1 to 30 mass % of a polymer having a silicone structure in which a ratio of deformation 0.3 or more and 1 or less, and in a bend resistance test using a cylindrical mandrel method, the minimum diameter of a cylindrical mandrel which causes no cracks in the polymer film is 2 mm or more and 25 mm or less; (B) a volatile oil having a volatilization rate of 14% or more after drying at 1 atmosphere, 40° C., and R.H. of 60% for 30 minutes; and (C) a powder comprising from 0.1 to 30 mass % of at least an inorganic powder having a refractive index of from 1.3 to 1.8. The mass ratio of the component (A) to the component (C), (A)/(C), is from 1 to 50.

4 Claims, 1 Drawing Sheet

(56) References Cited

OTHER PUBLICATIONS

Extended European Search Report issued Feb. 20, 2024, in corresponding European Patent Application No. 20907470.7, 11 pages.
International Search Report issued Mar. 9, 2021 in PCT/JP2020/047244, filed on Dec. 17, 2020, 2 pages.

* cited by examiner

COMPOSITION FOR SKIN EXTERNAL APPLICATION

CROSS-REFERENCE TO RELATED APPLICATIONS

The present application is a 35 U.S.C. § 371 national stage application of International patent application PCT/JP2020/047244, filed Dec. 17, 2020, which is based on and claims the benefit of priority to Japanese Application No. 2019-238768, filed Dec. 27, 2019. The entire contents of these applications are incorporated herein by reference.

FIELD OF THE INVENTION

The present invention relates to a composition for external preparation for skin.

BACKGROUND OF THE INVENTION

Human skin has more wrinkles with aging. This is part of an aging phenomenon of the skin and depends on multiple factors such as change in skin tissues and effect of exposure to an ultraviolet ray.

Conventionally, skin care products and the like for making skin wrinkles less noticeable have been studied. However, these products have an extremely low improving effect and have failed to gain satisfaction from women who have trouble of wrinkles.

Meanwhile, cosmetics compounded with a film-forming polymer are known which are intended to improve the uniformity of a makeup film and the makeup lasting quality. For example, Patent Literature 1 describes that a cosmetic containing a film-forming polymer in which a predetermined functional group is introduced into the skeleton of a polycycloolefin polymer allows makeup to last and achieves a favorable feel.

(Patent Literature 1) JP-A-2012-17317

SUMMARY OF THE INVENTION

The present invention relates to a composition for external preparation for skin comprising the following components (A), (B), and (C):

(A) from 1 to 30 mass % of a polymer having a silicone structure in which a ratio of deformation measured by the following method (1) is 0.3 or more and 1 or less, and in a bend resistance test using a cylindrical mandrel method performed by the following method (2), a minimum diameter of a cylindrical mandrel which causes no cracks in the polymer film is 2 mm or more and 25 mm or less:

Method (1): A 10 mass % hexamethyldisiloxane solution of the polymer is prepared. 0.005 g of the solution is applied to an area of 20 mm width×50 mm length on one side of a polyethylene sheet of 20 mm width×100 mm length×0.03 mm thickness in the length direction from one end of a short side, and the polyethylene sheet is dried in a thermostatic oven set at 40° C. for 10 minutes. Assuming the length of the polyethylene sheet portion coated with the solution as L1 and the length of a polyethylene sheet portion deformed by shrinkage after drying as L2, the value of L2/L1 is defined as a ratio of deformation;

Method (2): A 30 mass % hexamethyldisiloxane solution of the polymer is prepared. The solution is applied to a polyethylene terephthalate film of 50 mm width×100 mm length×0.1 mm thickness using a 200 μm applicator, and the film is dried in a thermostatic oven set at 40° C. for 120 minutes to prepare a test piece. A bend resistance test is performed using the test piece in accordance with a cylindrical mandrel method defined in JIS K5600-5-1:1999 to obtain the minimum diameter of a cylindrical mandrel which causes no cracks in the polymer film on the test piece, (B) a volatile oil having a volatilization rate of 14% or more after drying at 1 atmosphere, 40° C., and R.H. of 60% for 30 minutes, and (C) a powder, wherein a mass ratio of the component (A) to the component (C), (A)/(C), is from 1 to 50, wherein from 0.1 to 30 mass % of at least (C-1) an inorganic powder having a refractive index of from 1.3 to 1.8 is comprised as the component (C) in the composition.

DETAILED DESCRIPTION OF THE INVENTION

Conventional cosmetics containing a film-forming polymer have problems such as an insufficient wrinkle improving effect, a shiny, unnatural finish, and a noticeable boundary between the coating film and bare skin.

The present inventors found that a composition for external preparation for skin which maintains high shrinkage, improves wrinkles, suppresses shininess, and achieves a natural, matte finish and a less noticeable boundary between the coating film and bare skin could be obtained by using a specific proportion of an inorganic powder having a specific refractive index in a specific film-forming polymer, and accomplished the present invention.

The composition for external preparation for skin of the present invention can improve skin wrinkles, as well as suppresses shininess and achieves a fine, natural, matte, uniform finish and a less noticeable boundary between the coating film and bare skin.

In the present specification, the term "skin wrinkles" means roughness or folds that occur on the skin surface, which are changes in the shape that occur because of sagging of the skin. Skin wrinkles are likely to occur around the mouth and the eyes, on the forehead, the neck, and the body, and the like. Small folds are fine wrinkles, and large folds are large wrinkles, which occur with a flow of enlarged skin pores of nasolabial folds, cheek folds, and the like. The composition for external preparation for skin of the present invention exhibits an effect of making both types of wrinkles less noticeable and can improve even large wrinkles, such as nasolabial folds, in particular, in a noninvasive manner.

<Component (A)>

The component (A) used in the present invention is a polymer having a silicone structure in which a ratio of deformation measured by the method (1) is 0.3 or more and 1 or less, and in a bend resistance test using a cylindrical mandrel method performed by the method (2), the minimum diameter of a cylindrical mandrel which causes no cracks in the polymer film is 2 mm or more and 25 mm or less.

When the component (A) satisfies the above-mentioned ratio of deformation measured by the method (1), for example, a composition containing a polymer which is the component (A) is used by applying it to the skin surrounding wrinkles by coating or the like, and then when the composition is dried, shrinkage of the film containing the polymer occurs as well as the skin surface attached to the film. Because the skin portion with wrinkles is stretched by this action, wrinkles can be made less noticeable.

Figure 1:
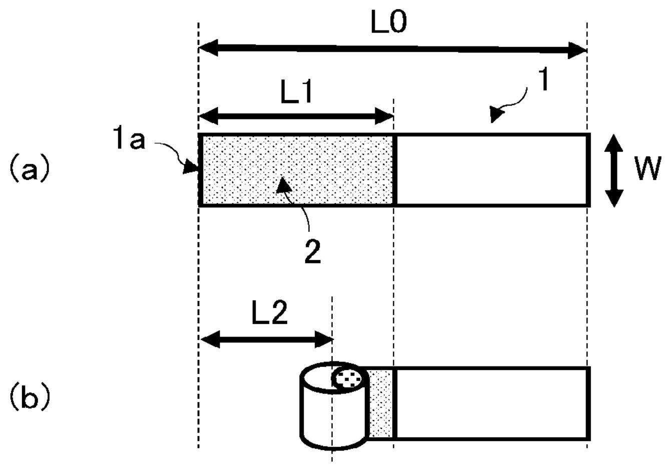
FIG. 1 is a diagram explaining a method for assessing the ratio of deformation (L2/L1) of a polymer by the method (1).

The method for assessing the ratio of deformation (L2/L1) of the component (A) by the method (1) is explained below with reference to FIG. 1. First, a 10 mass % hexamethyldisiloxane solution of the component (A) used for the composition is prepared. 0.005 g of this solution is applied to an area of 20 mm width×50 mm length (a portion of 2 shown in FIG. 1 (*a*)) on one side of a polyethylene sheet 1 of 20 mm width (W)×100 mm length (L0)×0.03 mm thickness shown in FIG. 1 (*a*) in the length direction from one end 1*a* of a short side of the polyethylene sheet 1, and the polyethylene sheet is dried in a thermostatic oven set at 40° C. for 10 minutes. FIG. 1 (*b*) is a schematic view showing that the polyethylene sheet 1 coated with the solution was dried, and then a portion thereof was deformed (curled) by shrinkage of the polymer which was the component (A).

Assuming the length of the polyethylene sheet portion coated with the solution as L1 (50 mm) and the length of the polyethylene sheet portion deformed by shrinkage after drying in the dried polyethylene sheet (FIG. 1 (*b*)) as L2, L2/L1 is calculated, and the value is defined as a ratio of deformation. L2 is defined as the mean value of lengths calculated for two long sides of the polyethylene sheet. A larger L2/L1 value means a greater degree of polymer shrinkage due to dryness, and the upper limit of L2/L1 is 1.

In view of smoothing skin wrinkles to make them less noticeable, the ratio of deformation, L2/L1, of the component (A) assessed by the method (1) is 0.3 or more, preferably 0.5 or more, more preferably 0.6 or more, even more preferably 0.7 or more, even more preferably 0.8 or more, even more preferably 0.85 or more, even more preferably 0.9 or more, even more preferably 0.95 or more, and the upper limit thereof is 1.

Specifically, the ratio of deformation can be assessed by the methods described in the examples.

Further, the component (A) has excellent bend resistance, and in a bend resistance test using a cylindrical mandrel method performed by the method (2), the minimum diameter of the cylindrical mandrel which causes no cracks in a film of a polymer which is the component (A) is 2 mm or more and 25 mm or less. With this diameter, a film formed by a composition containing the component (A) is unlikely to crack and likely to shrink while following the skin shape.

A smaller minimum diameter of the cylindrical mandrel means more favorable bend resistance. In view of achieving sufficient adhesiveness between a film containing the polymer and the skin surface during shrinkage of the film, the minimum diameter is 25 mm or less, preferably 20 mm or less, more preferably 12 mm or less, even more preferably 8 mm or less, even more preferably 6 mm or less, even more preferably 5 mm or less. Meanwhile, in view of imparting sufficient strength and a shape controlling effect to smooth skin wrinkles and make them less noticeable, the minimum diameter of the cylindrical mandrel which causes no cracks is 2 mm or more, preferably 3 mm or more. The specific range of the minimum diameter of the cylindrical mandrel is from 2 to 25 mm, preferably from 2 to 20 mm, more preferably from 2 to 12 mm, even more preferably from 2 to 8 mm, even more preferably from 3 to 6 mm, even more preferably from 3 to 5 mm.

The bend resistance can be assessed using a type 1 bend tester defined in JIS K5600-5-1:1999, specifically by the methods described in the examples.

Further, for the component (A), the ratio of the ratio of deformation obtained by the method (1) to the minimum diameter (mm) of the mandrel obtained by the method (2) [(ratio of deformation)/(minimum diameter of the mandrel)] is preferably 0.01 or more, more preferably 0.02 or more, even more preferably 0.10 or more, even more preferably 0.15 or more in view of a skin wrinkle improving effect; and is preferably 0.5 or less, more preferably 0.4 or less in view of imparting strength and the shape controlling effect sufficient to smooth skin wrinkles and make them less noticeable. A specific range of the ratio is preferably from 0.01 to 0.5, more preferably from 0.02 to 0.5, even more preferably from 0.10 to 0.5, even more preferably from 0.15 to 0.5, even more preferably from 0.15 to 0.4.

In the present invention, the term "silicone structure" refers to a structure of the following formula (I):

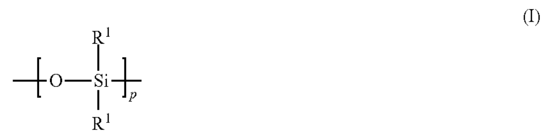

(I)

In the formula (I), $R^1$ is each independently a hydrocarbon group having one or more and 12 or less carbon atoms, and p is an integer of 1 or more. In view of smoothing skin wrinkles to make them less noticeable and achieving a sufficient wrinkle improving effect (hereinafter, also referred to as "skin wrinkle improving effect") and in view of versatility when used, $R^1$ is preferably an alkyl group having one or more and 12 or less carbon atoms or an aryl group having six or more and 12 or less carbon atoms, more preferably an alkyl group having one or more and 12 or less carbon atoms or a phenyl group, even preferably an alkyl group having one or more and three or less carbon atoms, even more preferably methyl group.

It is sufficient that the polymer which is the component (A) has a silicone structure, and the polymer may be a polymer consisting of a silicone structure alone. In view of preparing a polymer having the predetermined characteristics, however, a polymer having a silicone structure as a part thereof is preferred.

When a polymer has a silicone structure as a part thereof, the silicone structure may exist in either the main chain or a side chain of the polymer and preferably exists in a side chain in view of preparing a polymer having the predetermined characteristics.

When the silicone structure exists in the main chain of a polymer, the binding form is not particularly limited, and for example, the silicone structure may exist at the end of the main chain of the polymer, or the polymer may be a copolymer in which the silicone structure binds to the main chain of a polymer in a block or at random. Further, a graft-modified polymer with a compound having a silicone structure can be used.

The component (A) used in the present invention is preferably a silicone-modified polymer, and specific examples thereof include norbornane structure-containing silicone-modified polymers, such as silicone-modified polynorbornenes; silicone-modified Pullulans; silicone structure-containing silicic acid compounds, such as trialkylsiloxysilicic acid, fluorine-modified alkylsiloxysilicic acid, and phenyl-modified alkylsiloxysilicic acid; and silicone dendrimers.

(Norbornane Structure-Containing Silicone-Modified Polymers)

In the present invention, a norbornane structure means a structure of the following formula. It is sufficient that the norbornane structure-containing silicone-modified polymer is a silicone-modified polymer having the structure of the following formula at an arbitrary site in the polymer.

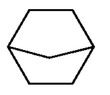

Examples of norbornane structure-containing silicone-modified polymers include polymers having a repeating unit of the following formula (1) or (2):

(1)

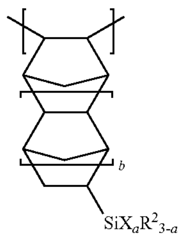

wherein $R^2$ is each independently an alkyl group having one or more and 12 or less carbon atoms, X is a group of the following formula (i). a is an integer of 1 or more and 3 or less, and b is an integer of 0 or more and 2 or less.

(i)

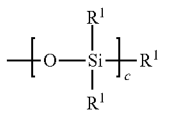

wherein $R^1$ is the same as described above, and c is an integer of 1 or more and 5 or less.

(2)

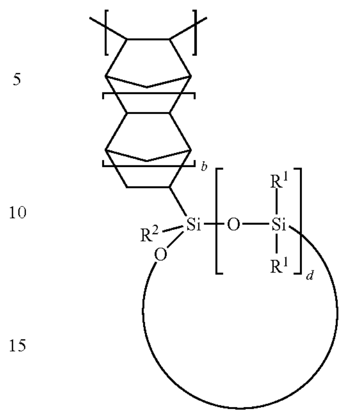

wherein $R^1$, $R^2$, and b are the same as described above, and d is an integer of 2 or more and 5 or less.

In the formula (1), $R^2$ is each independently an alkyl group having one or more and 12 or less carbon atoms, and in view of the skin wrinkle improving effect and in view of versatility, $R^2$ is preferably methyl group, ethyl group, n-propyl group, butyl group, or pentyl group, more preferably methyl group.

X is a group of the formula (i). In the formula (i), $R^1$ is each independently a hydrocarbon group having one or more and 12 or less carbon atoms. In view of the skin wrinkle improving effect and in view of versatility, $R^1$ is preferably an alkyl group having one or more and 12 or less carbon atoms or an aryl group having six or more and 12 or less carbon atoms, more preferably an alkyl group having one or more and 12 or less carbon atoms or a phenyl group, even preferably an alkyl group having one or more and three or less carbon atoms, even more preferably methyl group. c is an integer of 1 or more and 5 or less, and in view of versatility, c is preferably equal to 1. Specifically, X is preferably a trimethylsiloxy group.

a is an integer of 1 or more and 3 or less, and the polymer may be, for example, a polymer having a mixture of a repeating unit with a being 2 and a repeating unit with a being 3. In view of versatility, a is preferably 3. b is an integer of 0 or more and 2 or less, and in the same view, b is preferably 0, 1, or a combination thereof, more preferably 0.

In the formula (2), $R^1$, $R^2$, and b are the same as described above. d is an integer of 2 or more and 5 or less, and in view of versatility, d is preferably equal to 2. In the cyclic silicone structure in the formula (2), it is preferred in the same view that $R^1$ and $R^2$ are methyl group, and that d is 2 or 3. Specifically, the cyclic silicone structure in the formula (2) is preferably a structure of the following formula (4) or (5):

(4)

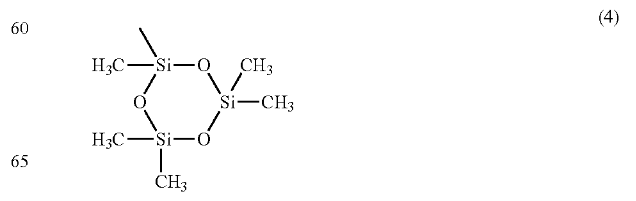

-continued (5)

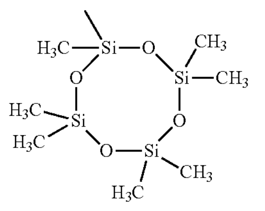

In view of the skin wrinkle improving effect, the proportion of repeating units of the formula (1) or (2) in a norbornane structure-containing silicone-modified polymer is preferably 10% or more, more preferably 30% or more, even more preferably 50% or more of the number of all repeating units in the polymer. The upper limit is 100%, and the proportion is preferably 95% or less, more preferably 90% or less, even preferably 70% or less. In a norbornane structure-containing silicone-modified polymer, the specific range of the number of repeating units of the formula (1) or (2) is preferably from 10% to 100%, more preferably from 10% to 95%, even preferably from 30% to 90%, even more preferably from 50% to 70% of the number of all repeating units in the polymer.

A norbornane structure-containing silicone-modified polymer may have a repeating unit of the following formula (3) in addition to the repeating unit of the formula (1) or (2)

(3)

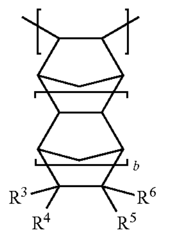

wherein $R^3$ to $R^6$ are each independently a substituent group selected from the group consisting of a hydrogen atom, a halogen atom, an alkyl group, an alkenyl group, a cycloalkyl group, an aryl group, an alkoxy group, an aryloxy group, and a halogenated hydrocarbon group which have one or more and 10 or less carbon atoms, an oxetanyl group, an alkoxycarbonyl group, a polyoxyalkylene group, a polyglyceryl group, and an alkoxysilyl group. Two groups selected from the group consisting of $R^3$ to $R^6$ may bond to each other to form an aliphatic ring structure, an aromatic ring structure, a carboimide group, or an acid anhydride group. b is the same as described above.

In view of the skin wrinkle improving effect, the proportion of the above-described repeating units of the formula (3) in a norbornane structure-containing silicone-modified polymer is preferably 90% or less, more preferably 70% or less, even more preferably 50% or less of the number of all repeating units in the polymer. Further, when the above-described repeating units of the formula (3) are contained, the proportion thereof is preferably 5% or more, more preferably 10% or more, even more preferably 30% or more of the number of all repeating units in the polymer. In a norbornane structure-containing silicone-modified polymer, the specific range of the number of repeating units of the formula (3) is preferably from 5% to 90%, more preferably from 10% to 70%, even more preferably from 30% to 50% of the number of all repeating units in the polymer.

The proportion of the above-described repeating units of the formulas (1) to (3) in a norbornane structure-containing silicone-modified polymer can be obtained by $^1$H-NMR measurement.

The norbornane structure-containing silicone-modified polymer is preferably a silicone-modified polynorbornene, more preferably a silicone-modified polynorbornene of the following formula (6):

(6)

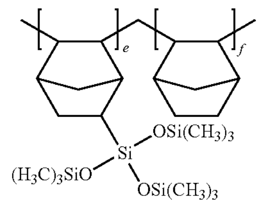

wherein e and f are the number of repeating units and are each independently an integer of 1 or more.

In view of the skin wrinkle improving effect, the ratio of e and f, e/f, in the formula (6) is preferably from 20/80 to 90/10 (mol/mol), more preferably from 30/70 to 80/20 (mol/mol), even more preferably from 50/50 to 70/30 (mol/mol).

In view of balancing shrinkage and bend resistance and in view of the skin wrinkle improving effect, the number average molecular weight (Mn) of a norbornane structure-containing silicone-modified polymer is preferably 50,000 or more, more preferably 100,000 or more, even more preferably 200,000 or more, and preferably 2,000,000 or less, more preferably 1,500,000 or less, even preferably 800,000 or less, even more preferably 600,000 or less. The specific range of the number average molecular weight (Mn) of a norbornane structure-containing silicone-modified polymer is preferably from 50,000 to 2,000,000, more preferably from 100,000 to 1,500,000, even preferably from 200,000 to 800,000, even more preferably from 200,000 to 600,000.

The number average molecular weight (Mn) of the polymer can be measured by gel filtration chromatography (GPC) using polystyrene as a reference substance, and specifically by the methods described in the examples.

The norbornane structure-containing silicone-modified polymer can be obtained by, for example, a known method of addition polymerization of a silicone-modified cyclic olefin monomer which comprises a norbornane structure or can form a norbornane structure.

For example, the above-described norbornane structure-containing silicone-modified polymer having the repeating unit of the formula (1) or (2) can be obtained by addition polymerization of a cyclic olefin monomer of the following formula (1a) or (2a). Further, a cyclic olefin monomer of the formula (3a) may be copolymerized.

(1a)

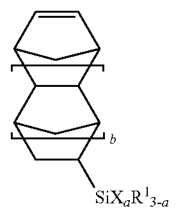

wherein $R^1$ is each independently an alkyl group having one or more and 12 or less carbon atoms, and X is a group of the following formula (i). a is an integer of 1 or more and 3 or less, and b is an integer of 0 or more and 2 or less.

(i)

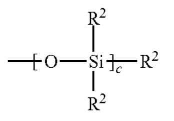

wherein $R^2$ is each independently a hydrocarbon group having one or more and 12 or less carbon atoms, and c is an integer of 1 or more and 5 or less.

(2a)

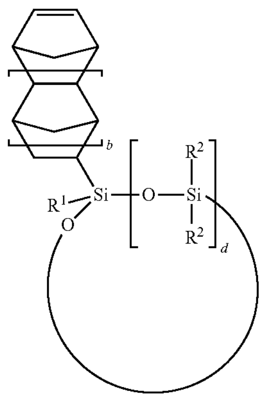

wherein $R^1$, $R^2$, and b are the same as described above, and d is an integer of 2 or more and 5 or less.

(3a)

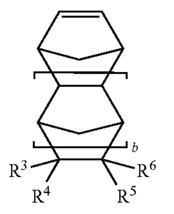

wherein $R^3$ to $R^6$ are each independently a substituent group selected from the group consisting of a hydrogen atom, a halogen atom, an alkyl group, an alkenyl group, a cycloalkyl group, an aryl group, an alkoxy group, an aryloxy group, and a halogenated hydrocarbon group which have one or more and 10 or less carbon atoms, an oxetanyl group, an alkoxycarbonyl group, a polyoxyalkylene group, a polyglyceryl group, and an alkoxysilyl group. Two groups selected from the group consisting of $R^3$ to $R^6$ may bind to each other to form an aliphatic ring structure, an aromatic ring structure, a carboimide group, or an acid anhydride group. b is the same as described above.

When the above-described cyclic olefin monomer of the formula (3a) is copolymerized, the use amount thereof is, in view of the skin wrinkle improving effect, preferably 90 mol % or less, more preferably 70 mol % or less, even more preferably 50 mol % or less, and preferably 5 mol % or more, more preferably 10 mol % or more, even more preferably 30 mol % or more, assuming the amount of all monomers used for polymerization as 100 mol %.

The above-described silicone-modified polynorbornene of the formula (6) can be obtained by addition polymerization of tris(trimethylsiloxy)silylnorbornene of the following formula (6a) and norbornene:

(6a)

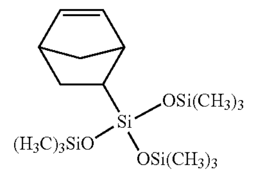

In view of the skin wrinkle improving effect, the copolymerization ratio of tris(trimethylsiloxy)silylnorbornene and norbornene is preferably from 20/80 to 90/10 (mol/mol), more preferably from 30/70 to 80/20 (mol/mol), even more preferably from 50/50 to 70/30 (mol/mol).

Of note, all the repeating units of the formulas (1) to (3) and (6) represent a unit of a 2,3-addition structure of a cyclic olefin monomer as a raw material monomer and may contain a unit of a 2,7-addition structure obtained by addition polymerization of the cyclic olefin monomer.

The norbornane structure-containing silicone-modified polymer is preferably a norbornene/tris(trimethylsiloxy)silylnorbornene copolymer, i.e., a compound which is expressed as NORBORNENE/TRIS(TRIMETHYLSILOXY)SILYLNORBORNENE COPOLYMER, as the INCI name (International Cosmetic Ingredient Dictionary and Handbook, 16th Edition, Volume 2, 2016, p. 2274).

Examples of commercially available norbornane structure-containing silicone-modified polymers include "NBN-30-ID" (an isododecane solution of a norbornene/tris(trimethylsiloxy)silylnorbornene) copolymer) manufactured by Shin-Etsu Chemical Co., Ltd.

(Silicone-Modified Pullulans)

Examples of silicone-modified Pullulans include Pullulans having a silicone structure in a side chain. Specifically, in view of the skin wrinkle improving effect and in view of versatility, a silicone-modified Pullulan in which at least some hydrogen atoms of an OH group in the Pullulan is substituted with a group of the following formula (7) is preferred:

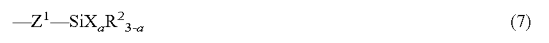

$-Z^1-SiX_aR^2_{3-a}$ (7)

wherein $Z^1$ is a single bond or divalent organic group. $R^2$, X, and a are the same as described above, and in the same view, X is preferably trimethylsiloxy group, and a is preferably 3.

In the same view, in the formula (7), $Z^1$ is preferably a divalent organic group, more preferably a divalent group of the following formula (8) or (9), even more preferably a divalent group of the following formula (9).

(8)

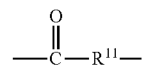

(9)

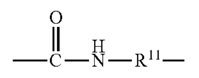

wherein $R^{11}$ is an alkylene group having one or more and 10 or less carbon atoms, and examples thereof include methylene group, ethylene group, trimethylene group, propylene group, and butylene group. Of these, in the same view, ethylene group, trimethylene group, and propylene group are preferred, and trimethylene group and propylene group are more preferred.

Examples of commercially available silicone-modified Pullulans include "TSPL-30-ID" (an isododecane solution of tri(trimethylsiloxy)silyl propyl carbamide acid Pullulan) and "TSPL-30-D5" (a cyclopentasiloxane solution of tri (trimethylsiloxy)silyl propyl carbamide acid Pullulan), which are manufactured by Shin-Etsu Chemical Co., Ltd.

(Silicone Structure-Containing Silicic Acid Compounds)

Examples of the silicone structure-containing silicic acid compound used in the present invention include silicate compounds having a silicone structure at an end thereof, and examples thereof include trialkylsiloxysilicic acids, fluorine-modified alkylsiloxysilicic acids, and phenyl-modified alkylsiloxysilicic acids.

In view of the skin wrinkle improving effect and in view of versatility, an alkyl group in a trialkylsiloxysilicic acid has preferably one or more and 10 or less carbon atoms, more preferably one or more and four or less carbon atoms, and is even preferably methyl group. Specific examples of trialkylsiloxysilicic acids include trimethylsiloxysilicic acid.

Examples of fluorine-modified alkylsiloxysilicic acids include compounds in which at least some hydrogen atoms in an alkyl group in a trialkylsiloxysilicic acid are substituted with a fluorine atom. Specific examples thereof include trifluoropropyldimethylsiloxysilicic acid and trifluoropropyldimethyl/trimethylsiloxysilicic acid.

Examples of phenyl-modified alkylsiloxysilicic acids include phenylpropyldimethylsiloxysilicic acid and phenylpropyldimethyl/trimethylsiloxysilicic acid.

In view of the skin wrinkle improving effect, one or more selected from the group consisting of trialkylsiloxysilicic acids and fluorine-modified alkylsiloxysilicic acids are preferred among the silicone structure-containing silicic acid compounds.

Examples of commercially available silicone structure-containing silicic acid compounds include trimethylsiloxysilicic acids (solution), such as "KF-7312J," "KF-7312K," "KF-7312T," "KF-7312L," "X-21-5249," "X-21-5250," "KF-9021," "X-21-5595," "X-21-5616," "KF-9021L," "X-21-5249L," and "X-21-5250L," which are manufactured by Shin-Etsu Chemical Co., Ltd., and "XS66-B8226" (a cyclopentasiloxane solution of trifluoropropyldimethyl/trimethylsiloxysilicic acid), "XS66-B8636" (a dimethicone solution of trifluoropropyldimethyl/trimethylsiloxysilicic acid), and "SilShine 151" (phenylpropyldimethylsiloxysilicic acid), which are manufactured by Momentive Performance Materials Japan LLC.

(Silicone Dendrimers)

Examples of silicone dendrimers include vinyl polymers having a siloxane dendrimer structure in a side chain thereof. Specifically, in view of the skin wrinkle improving effect and in view of versatility, the siloxane dendrimer structure is preferably a group of the following formula (10):

(10)

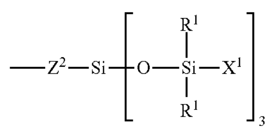

wherein $R^1$ is the same as described above. $Z^2$ is a single bond or divalent organic group. $X^1$ is a group of the following formula (11) when i is equal to 1, and i is an integer of 1 or more and 10 or less, indicating the hierarchy of the group:

(11)

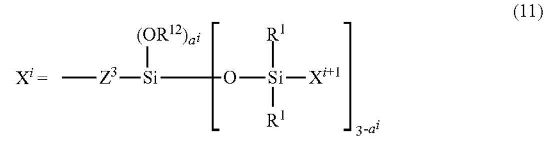

wherein $R^1$ is the same as described above, and $R^{12}$ is an alkyl group having one or more and 10 or less carbon atoms. $Z^3$ is an alkylene group having two or more and 10 or less carbon atoms. $X^{i+1}$ is a hydrogen atom, an alkyl group having one or more and 10 or less carbon atoms, an aryl group, or a group of the formula (11), and $a^i$ is an integer of 0 or more and 3 or less.

In the formula (10), $Z^2$ is a single bond or divalent organic group, in view of versatility, preferably a divalent organic group, more preferably a divalent group of the following formula (12), (13), or (14):

(12)

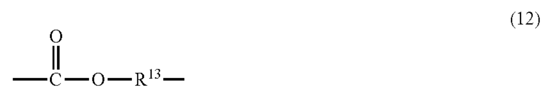

(13)

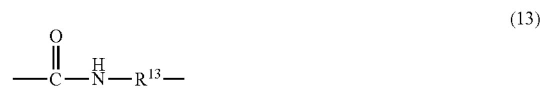

(14)

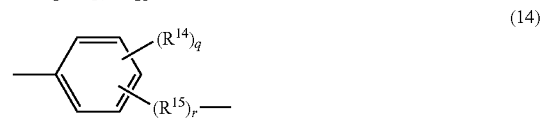

wherein $R^{13}$ is an alkylene group having one or more and 10 or less carbon atoms, and examples thereof include methylene group, ethylene group, trimethylene group, propylene group, and butylene group. In view of versatility, ethylene group, trimethylene group, and propylene group are preferred. $R^{14}$ is an alkyl group having one or more and 10 or less carbon atoms, and examples thereof include methyl group, ethyl group, propyl group, and butyl group. In the same view, methyl group is preferred. $R^{15}$ is an alkylene group having one or more and 10 or less carbon atoms, and examples thereof include methylene group, ethylene group, trimethylene group, propylene group, and butylene group. In the same view, ethylene group is preferred. q is an integer of 0 or more and 4 or less, and r is 0 or 1.

Examples of vinyl polymers having the above-described siloxane dendrimer structure in a side chain (hereinafter, also referred to simply as "vinyl polymer") include polymers having a repeating unit derived from a monomer of the following formula (15):

(15)

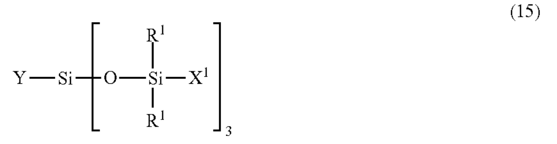

wherein $R^1$ and $X^1$ are the same as described above. Y is a group containing a vinyl bond, and examples thereof include vinyl group, 2-acryloyloxyethyl group, 3-acryloyloxypropyl group, 2-methacryloyloxyethyl group, 3-methacryloyloxypropyl group, 4-vinylphenyl group, 3-vinylphenyl group, 4-(2-propenyl)phenyl group, 3-(2-propenyl)phenyl group, 2-(4-vinylphenyl)ethyl group, 2-(3-vinylphenyl)ethyl group, allyl group, and 5-hexenyl group. Of these, in view of versatility, (meth)acryloyl group and vinyl group are preferred, and (meth)acryloyl group is more preferred.

The vinyl polymer may further contain a repeating unit derived from a vinyl monomer other than the monomer of the formula (15). Examples of such vinyl monomers include monomers which have a group having a vinyl bond and are not the monomer of the formula (15), and examples thereof include (meth)acrylic acid, alkyl(meth)acrylate, hydroxyalkyl(meth)acrylate, aromatic ring-containing (meth)acrylate, fatty acid vinyl esters, (meth)acrylamide, styrene, and derivatives thereof. One or more of these can be used. Of these, (meth)acryl monomers, such as (meth)acrylic acid, alkyl(meth)acrylate, hydroxyalkyl(meth)acrylate, and aromatic ring-containing (meth)acrylate, are preferred in view of versatility.

In view of the skin wrinkle improving effect, the content of a repeating unit derived from the monomer of the formula (15) in a vinyl polymer is preferably 0.1 mass % or more, more preferably 10 mass % or more, even more preferably 20 mass % or more of all repeating units in the vinyl polymer. The upper limit is 100 mass %.

The vinyl polymer is more preferably an acrylic polymer. Specifically, preferred examples of silicone dendrimers include an acrylic polymer having a siloxane dendrimer structure in a side chain (hereinafter, also referred to as "acryl silicone dendrimer"). An acryl silicone dendrimer is a polymer having a repeating unit derived from a monomer in which Y is a (meth)acryloyl group in the formula (15) and may further contain a repeating unit derived from a (meth)acrylic monomer other than the monomer of formula (15).

Examples of commercially available silicone dendrimers include acrylic silicone dendrimers, such as "FA 4001 CM Silicone Acrylate" (a cyclopentasiloxane solution of acrylate-polytrimethylsiloxymethacrylate copolymer) and "FA 4002 ID Silicone Acrylate" (an isododecane solution of acrylate-polytrimethylsiloxymethacrylate copolymer), which are manufactured by Dow Corning Toray Co., Ltd.

In view of the skin wrinkle improving effect, among the above-mentioned polymers, the component (A) is preferably one or more selected from the group consisting of silicone-modified polynorbornenes, silicone-modified Pullulans, trimethylsiloxysilicic acid, trifluoropropyldimethyl/trimethylsiloxysilicic acid, and acrylic silicone dendrimers, more preferably one or more selected from the group consisting of silicone-modified polynorbornenes, silicone-modified Pullulans, trimethylsiloxysilicic acid, and trifluoropropyldimethyl/trimethylsiloxysilicic acid. In view of the skin wrinkle improving effect and in view of bend resistance, one or more selected from the group consisting of silicone-modified polynorbornenes and silicone-modified Pullulans are even preferred, and silicone-modified polynorbornenes are even more preferred.

One or more different components (A) can be used in combination, and in view of the skin wrinkle improving effect, the content thereof in the whole composition is 1 mass % or more, preferably 2 mass % or more, more preferably 4 mass % or more, even more preferably 5 mass % or more, and is 30 mass % or less, preferably 25 mass % or less, more preferably 20 mass % or less, even more preferably 18 mass % or less. Further, the content of the component (A) in the whole composition is from 1 to 30 mass %, preferably from 2 to 25 mass %, more preferably from 4 to 20 mass %, further preferably from 5 to 18 mass %.

<Component (B)>

The component (B) used in the present invention is a volatile oil with a volatilization rate of 14% or more after drying at 1 atmosphere, 40° C., and R.H. of 60% for 30 minutes. Since the drying speed of a composition containing the component (A) is improved when the component (B) is added, shrinkage of the component (A) is accelerated during the drying process, leading to improvement in the effect of smoothing skin wrinkles to make them less noticeable.

In view of obtaining the above-described effects, the volatilization rate of the component (B) after drying at 1 atmosphere, 40° C., and R.H. of 60% for 30 minutes is preferably 18% or more, more preferably 25% or more, even preferably 30% or more, even more preferably 45% or more, even more preferably 65% or more, even more preferably 80% or more, even more preferably 95% or more. The upper limit is 100%.

After placing 0.5 g of a sample in a glass petri dish of 40 mm in diameter and leaving and drying it in an environment of 1 atmosphere, R.H. of 60%, and 40° C. for 30 minutes, the volatilization rate of the component (B) is obtained as a value of $\{(W_0-W_1)/W_0\}\times100$ assuming the sample mass before drying as $W_0$ (g) and the sample mass after drying as $W_1$ (g). A greater value means a faster volatilization speed, resulting in easily getting dry.

Of note, two or more different volatile oils may be used as the component (B).

The above-described volatilization rate can be specifically measured by the methods described in the examples.

In view of increasing the skin wrinkle improving effect, examples of the component (B) include one or more oil solutions selected from the group consisting of hydrocarbon oils and silicone oils which have a volatilization rate within the above-mentioned range. Of these, one or more selected from the group consisting of isododecane (volatilization rate, 33%), hexamethyldisiloxane (volatilization rate, 100%), methyl trimethicone, and polydimethylsiloxane having kinematic viscosity of 2 cSt or less at 25° C. are preferred. Of note, the kinematic viscosity can be measured by, for example, using an Ubbelohde's viscometer.

In view of increasing the skin wrinkle improving effect, the component (B) is more preferably one or more selected from the group consisting of isododecane, hexamethyldisiloxane, and polydimethylsiloxane having kinematic viscosity of 1.5 cSt or less at 25° C., even preferably one or more selected from the group consisting of hexamethyldisiloxane and polydimethylsiloxane having kinematic viscosity of 1 cSt or less at 25° C., even more preferably hexamethyldisiloxane.

Examples of commercially available hexamethyldisiloxane and polydimethylsiloxane having kinematic viscosity of 2 cSt or less at 25° C. include "KF-96L-0.65cs" (hexamethyldisiloxane), "TMF1.5," "KF-96L-1cs" (octamethyltrisiloxane), "KF-96L-1.5cs," and "KF-96L-2cs," which are manufactured by Shin-Etsu Chemical Co., Ltd., "SH200C Fluid 1cs" and "SH200C Fluid 1.5cs," which are manufactured by Dow Corning Toray Co., Ltd., "TSF451-0.65" manufactured by Momentive Performance Materials Japan LLC, and "BELSIL DM0.65" manufactured by Wacker Asahikasei Silicone Co., Ltd.

One or more different components (B) can be used in combination. In view of increasing the skin wrinkle improving effect, the content thereof is preferably 1 mass % or more, more preferably 30 mass % or more, even preferably 50 mass % or more, even more preferably 70 mass % or more, even more preferably 75 mass % or more, and preferably 99 mass % or less, more preferably 98 mass % or less, even preferably 97 mass % or less, even more preferably 94 mass % or less, even more preferably 92 mass % or less, even more preferably 90 mass % or less in the whole composition. Further, the content of the component (B) is preferably from 1 to 99 mass %, more preferably from 1 to 98 mass %, even preferably from 30 to 97 mass %, even more preferably from 50 to 94 mass %, even more preferably from 70 to 92 mass %, even more preferably from 75 to 90 mass % in the whole composition.

In the present invention, in view of the skin wrinkle improving effect, the mass ratio of the component (A) to the component (B), (A)/(B), is preferably 0.02 or more, more preferably 0.03 or more, even preferably 0.04 or more, even more preferably 0.05 or more, even more preferably 0.1 or more and preferably 1 or less, more preferably 0.7 or less, even preferably 0.4 or less, even more preferably 0.25 or less, even more preferably 0.24 or less. Further, the mass ratio of the component (A) to the component (B), (A)/(B), is preferably from 0.02 to 1, more preferably from 0.03 to 0.7, even preferably from 0.04 to 0.4, even more preferably from 0.05 to 0.25, even more preferably from 0.1 to 0.24.

<Component (C)>

The component (C) of the present invention is a powder and may be any of an organic powder, an inorganic powder, or the like.

Examples of organic powders include crosslinked or non-crosslinked organic powders such as polyamide resin, nylon resin, polyester resin, polyethylene resin, polytetrafluoroethylene resin, polypropylene resin, polystyrene resin, benzoguanamine resin, polymethylbenzoguanamine resin, polymethyl methacrylate, polyurethane resin, vinyl resin, fluorine resin, acrylic resin, and melamine resin; silicone resins such as silicone elastomers and polymethylsilsesquioxane in which dimethyl silicone are crosslinked; and one or more polymer or copolymer powders selected from the group consisting of poly(meth)acrylic acid, sodium poly(meth)acrylate, poly(meth)acrylate esters, and alkylene glycol poly(meth)acrylate, such as butyl acrylate-vinyl acetate copolymer, styrene-acrylic acid copolymer, divinylbenzene-styrene copolymer, and (lauryl methacrylate-ethylene glycol dimethacrylate) copolymer.

Examples of inorganic powders include talc, kaolin, mica, sericite, phlogopite, aluminium/magnesium silicate, calcium silicate, aluminium silicate, magnesium silicate, barium silicate, strontium silicate, epoxy-treated aluminium, aluminium powder, calcium phosphate, anhydrous silicic acid, anhydrous aluminium silicate, pyrophyllite-containing clay, bentonite, smectite, montmorillonite, vermiculite, hectorite, zeolite, Higilite, silica, alumina, zirconium, iron oxides (red iron oxide, yellow iron oxide, black iron oxide, γ-iron oxide), loess, black titanium oxide, lower-order titanium oxides, iron titanate, zinc oxide, aluminium hydroxide, aluminium oxide, aluminum cobalt oxide, chromium oxide, zirconium oxide, titanium oxide, titanium oxide sol, iron oxide-titanium dioxide sinter, cerium oxide, magnesium oxide, chromium hydroxide, titanium-titanium dioxide sinter, cobalt titanate, manganese violet, cobalt violet, calcium carbonate, barium carbonate, magnesium carbonate, metal tungstate, barium sulfate, calcined calcium sulfate (calcined gypsum), bismuth oxychloride, calamine, sodium resinate-treated magnesium oxide, fluoroapatite, hydroxyapatite, ceramic powder, and metal soaps (e.g., zinc myristate, calcium palmitate, aluminium stearate), and composite powders of two or more thereof. Examples of inorganic powders further include organic-inorganic composite powders such as acrylic resin-coated aluminium powder and titanium oxide-coated nylon powder.

Further, examples of natural fiber powders include silk powder, wool powder, and cellulose powder.

Examples of pearl gloss pigments include mica titanium, iron oxide-coated mica titanium, titanium oxide-coated bismuth oxychloride, titanium oxide-coated talc, titanium oxide-coated glass flakes, and fish scale foil.

In view of suppressing shininess, achieving a natural, matte, uniform finish, and preventing the boundary between the coating film and bare skin from becoming noticeable, the component (C) contains preferably at least (C-1) an inorganic powder having a refractive index of from 1.3 to 1.8, more preferably an inorganic powder having a refractive index of from 1.4 to 1.7, even more preferably an inorganic powder having a refractive index of from 1.4 to 1.6.

Examples of such an inorganic powder (C-1) include one or more selected from the group consisting of zeolite (refractive index, from 1.47 to 1.49), silica (refractive index, 1.54), talc (refractive index, from 1.54 to 1.59), sericite (refractive index, 1.58), mica (refractive index, 1.58), barium carbonate (refractive index, 1.6), barium sulfate (refractive index 1.64), hydroxyapatite (refractive index, 1.65), calcium carbonate (refractive index, 1.66), and alumina (refractive index, 1.77), preferably one or more selected from the group consisting of zeolite, silica, talc, sericite, mica, barium carbonate, barium sulfate, hydroxyapatite, and calcium carbonate, more preferably one or more selected from the group consisting of silica, sericite, mica, and barium sulfate.

In view of preventing the boundary between the coating film and bare skin from becoming noticeable without impairing the strength of the coating film on the skin after coating, the inorganic powder having a refractive index of from 1.3 to 1.8 which is the component (C-1) is preferably a hydrophobization-treated inorganic powder.

The hydrophobization treatment is not limited as long as it is treatment performed for usual cosmetic powders, and examples thereof include silicone treatment, alkoxy silane treatment, fatty acid treatment, lauroyl lysine treatment, lecithin treatment, N-acyl amino acid treatment, metal soap treatment, and fluorination treatment. Of these, silicone treatment is preferred. These treatments can be performed by usual methods.

In view of maintaining the skin wrinkle improving effect, suppressing shininess, achieving a natural, matte, uniform finish, and preventing the boundary between the coating film and bare skin from becoming noticeable, the content of such an inorganic powder which is the component (C-1) is 0.1 mass % or more, preferably 1 mass % or more, more preferably 2 mass % or more, even more preferably 3 mass % or more, and 30 mass % or less, preferably 15 mass % or less, more preferably 10 mass % or less, even more preferably 8 mass % or less in the whole composition. Further, the content of the component (C-1) is from 0.1 to 30 mass %, preferably from 1 to 15 mass %, more preferably from 2 to 10 mass %, even more preferably from 3 to 8 mass % in the whole composition.

In the present invention, in view of maintaining the skin wrinkle improving effect, suppressing shininess, achieving a natural, matte, uniform finish, and preventing the boundary between the coating film and bare skin from becoming noticeable, the mass ratio of the component (A) to the component (C-1), (A)/(C-1), is preferably 1 or more and preferably 50 or less, more preferably 22 or less, even more preferably 10 or less, even more preferably 5 or less. Further, the mass ratio of the component (A) to the component (C-1), (A)/(C-1), is preferably from 1 to 50, more preferably from 1 to 22, even more preferably from 1 to 10, even more preferably from 1 to 5.

Further, in view of suppressing shininess and preventing the boundary between the coating film and bare skin from becoming noticeable, the average particle diameter of the component (C) is preferably 0.01 μm or more, more preferably 0.1 μm or more, even more preferably 1 μm or more, and preferably 100 μm or less, more preferably 30 μm or less, even more preferably 15 μm or less. Further, the particle diameter of the component (C) is preferably from 0.01 to 100 μm, more preferably from 0.1 to 30 μm, even more preferably from 1 to 15 m.

In the present invention, the particle diameter is measured by electron microscopic observation and laser diffraction/scattering method using a particle size distribution measuring instrument. Specifically, in the laser diffraction/scattering method, measurement is performed with a laser diffraction scattering-type grain size distribution measuring instrument (e.g., HELOS & RODOS manufactured by Sympatec GmbH) having a dry measuring unit under a dispersive pressure of 0.1 bar.

One or more different components (C) can be used in combination, and in view of suppressing shininess of the finish, the whole content including the component (C-1) is preferably 0.1 mass % or more, more preferably 1 mass % or more, even preferably 2 mass % or more, even more preferably 3 mass % or more, and preferably 40 mass % or less, more preferably 20 mass % or less, even preferably 15 mass % or less, even more preferably 10 mass % or less in the whole composition. Further, the content of the component (C) is preferably from 0.1 to 40 mass %, more preferably from 1 to 20 mass %, even preferably from 2 to 15 mass %, even more preferably from 3 to 10 mass % in the whole composition.

In the present invention, in view of suppressing shininess of the finish, the mass ratio of the component (A) to the component (C), (A)/(C), is preferably 1 or more, and preferably 50 or less, more preferably 22 or less, even preferably 10 or less, even more preferably 5 or less. Further, the mass ratio of the component (A) to the component (C), (A)/(C), is preferably from 1 to 50, more preferably from 1 to 22, even preferably from 1 to 10, even more preferably from 1 to 5.

<Other Components>

The composition for external preparation for skin of the present invention can further contain a surfactant, and preferred examples thereof include anionic surfactants, cationic surfactants, nonionic surfactants, and ampholytic surfactants.

Surfactants are not limited as long as they are used for usual agents for skin external use, but they are preferably nonionic surfactants in view of being soluble in a volatile oil, and preventing stickiness.

Examples of nonionic surfactants include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene fatty acid ester, polyoxyethylene sorbitan fatty acid ester, polyoxyethylenealkyl ether, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene hydrogenated castor oil fatty acid ester, polyoxyethylene phytostanol ether, polyoxyethylene phytosterose ether, polyoxyethylene cholestanol ether, polyoxyethylene cholesteryl ether, alkyl glyceryl ether-modified silicone, polyoxyalkylene-modified silicone, polyoxyalkylene-alkyl co-modified silicone, and polyoxyalkylene-fluoroalkyl co-modified silicone.

Of these, in view of increasing dispersibility/solubility of water and water-soluble components in an oil, a nonionic surfactant preferably contains one or more alkyl glyceryl ether-modified silicones and polyoxyalkylene-modified silicones, more preferably polyoxyalkylene-modified silicones.

Examples of polyoxyalkylene-modified silicones which can be used include commercially available products such as SH3771M, SH3772M, SH3773M, SH3775M, SH3749, and DC5200, which are manufactured by Dow Corning Toray Co., Ltd, and KF-6011, KF-6012, KF-6013, KF-6015, KF-6016, KF6017, and KF-6004, which are manufactured by Shin-Etsu Chemical Co., Ltd.

In view of increasing dispersibility/solubility of water and water-soluble components in an oil, the HLB value of a nonionic surfactant is preferably 1 or more and 7 or less, more preferably 2 or more and 6 or less.

Here, HLB (Hydrophilic-Lipophilic Balance) represents the proportion of the molecular weight of a hydrophilic portion to the molecular weight of the whole surfactant and can be obtained by the Griffin's formula for nonionic surfactants.

The HLB value of a mixed surfactant composed of two or more nonionic surfactants is obtained as follows. The HLB of the mixed surfactant is obtained by calculating an arithmetic mean of the HLB values of each nonionic surfactant based on the mixing ratio.

$$\text{Mixed HLB}=\Sigma(\text{HLB}x\times Wx)/\Sigma Wx$$

HLBx represents the HLB value of a nonionic surfactant X.

Wx represents weight (g) of the nonionic surfactant X having the HLBx value.

One or more different nonionic surfactants can be used in combination, and in view of being soluble in a volatile oil and preventing stickiness, the content of the nonionic surfactants is preferably 30 mass % or less, more preferably 10 mass % or less, even preferably 5 mass % or less, further preferably 3 mass % or less, even more preferably 1 mass % or less in the whole composition.

In the present invention, in view of maintaining the skin wrinkle improving effect and obtaining a use impression of non-stickiness, the content of water is preferably 50 mass % or less, more preferably 30 mass % or less, even preferably 10 mass % or less, even more preferably 5 mass % or less, even more preferably 1 mass % or less in the whole composition.

In addition to the above-described components, the composition for the external preparation for skin of the present invention can optionally use various components usually used as long as the effect of the present invention is not impaired. Examples of these components include oily components other than described above, water-soluble polymers, antioxidants, ultraviolet absorbers, vitamins, preservatives, pH modifiers, flavors, plant extracts, moisturizers, colorants, cooling sensation agents, antiperspirants, sterilizers, and skin activators.

The composition for external preparation for skin of the present invention can be applied to any forms such as oily compositions and emulsified compositions which can be manufactured by usual methods. The composition for external preparation for skin of the present invention can be applied as a preparation such as a liquid, a milky lotion, a paste, a cream, a gel, a solid, or a sheet.

The composition for external preparation for skin of the present invention can be used for cosmetics, quasi-drugs, and drugs and can be used as skin care cosmetics such as lotions, milky lotions, creams, beauty essences, dispersions, gels, ointments, facial masks, mousses, aerosols, poultices, and cleansing agents; ultraviolet protection cosmetics such as sunscreen milky lotions and sunscreen creams; makeup cosmetics such as makeup bases, foundations, concealers, blushes, eye shadows, mascaras, eyeliners, eyebrows, overcoats, and lipsticks, and the like.

The composition for external preparation for skin of the present invention is suitable for use as a skin wrinkle improving agent.

Regarding the above-described embodiments, the present invention further discloses the following compositions.

<1> A composition for external preparation for skin comprising the following components (A), (B), and (C):

(A) from 1 to 30 mass % of a polymer having a silicone structure in which a ratio of deformation measured by the following method (1) is 0.3 or more and 1 or less, and in a bend resistance test using a cylindrical mandrel method performed by the following method (2), a minimum diameter of a cylindrical mandrel which causes no cracks in the polymer film is 2 mm or more and 25 mm or less:

Method (1): a 10 mass % hexamethyldisiloxane solution of the polymer is prepared. 0.005 g of the solution is applied to an area of 20 mm width×50 mm length on one side of a polyethylene sheet of 20 mm width×100 mm length×0.03 mm thickness in the length direction from one end of a short side, and the polyethylene sheet is dried in a thermostatic oven set at 40° C. for 10 minutes. Assuming the length of the polyethylene sheet portion coated with the solution as L1 and the length of the polyethylene sheet portion deformed by shrinkage after drying as L2, the value of L2/L1 is defined as a ratio of deformation;

Method (2): A 30 mass % hexamethyldisiloxane solution of the polymer is prepared. The solution is applied to a polyethylene terephthalate film of 50 mm width×100 mm length×0.1 mm thickness using a 200 m applicator, and the film is dried in a thermostatic oven set at 40° C. for 120 minutes to prepare a test piece. A bend resistance test is performed using the test piece in accordance with a cylindrical mandrel method defined in JIS K5600-5-1:1999 to obtain the minimum diameter of a cylindrical mandrel which causes no cracks in the polymer film on the test piece, (B) a volatile oil having a volatilization rate of 14% or more after drying at 1 atmosphere, 40° C., and R.H. of 60% for 30 minutes, and (C) a powder, wherein a mass ratio of the component (A) to the component (C), (A)/(C), is from 1 to 50, wherein from 0.1 to 30 mass % of at least (C-1) an inorganic powder having a refractive index of from 1.3 to 1.8 is comprised as the component (C) in the composition.

<2> The composition for external preparation for skin according to the above <1>, wherein, in the component (A) the ratio of deformation, L2/L1, assessed by the method (1) is preferably 0.5 or more, more preferably 0.6 or more, even preferably 0.7 or more, even more preferably 0.8 or more, even more preferably 0.85 or more, even more preferably 0.9 or more, even more preferably 0.95.

<3> The composition for external preparation for skin according to the above <1> or <2>, wherein, for the component (A), the minimum diameter of the cylindrical mandrel which causes no cracks in a polymer film which is the component (A) is preferably 20 mm or less, more preferably 12 mm or less, even preferably 8 mm or less, even more preferably 6 mm or less, even more preferably 5 mm or less, and preferably 3 mm or more in a bend resistance test using a cylindrical mandrel method performed by the method (2).

<4> The composition for external preparation for skin according to any one of the above <1> to <3>, wherein, for the component (A), a ratio of the ratio of deformation obtained by the method (1) to the minimum diameter (mm) of the mandrel obtained by the method (2) [(percent deformation)/(minimum diameter of the mandrel)] is preferably 0.01 or more, more preferably 0.02 or more, even preferably 0.10 or more, even more preferably 0.15 or more, and preferably 0.5 or less, more preferably 0.4 or less.

<5> The composition for external preparation for skin according to any one of the above <1> to <4>, wherein the component (A) is preferably a silicone-modified polymer, more preferably a norbornane structure-containing silicone-modified polymer, a silicone-modified Pullulan, a silicone structure-containing silicic acid compound, or a silicone dendrimer.

<6> The composition for external preparation for skin according to any one of the above <1> to <5>, wherein the component (A) is preferably a norbornane structure-containing silicone-modified polymer, more preferably a polymer having a repeating unit of the following formula (1) or (2):

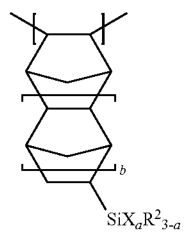

(1)

wherein $R^2$ is each independently an alkyl group having one or more and 12 or less carbon atoms, and X is a group of the following formula (i) a is an integer of 1 or more and 3 or less, and b is an integer of 0 or more and 2 or less.

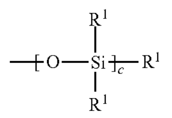

(i)

wherein $R^1$ is the same as described above, and c is an integer of 1 or more and 5 or less.

(2)

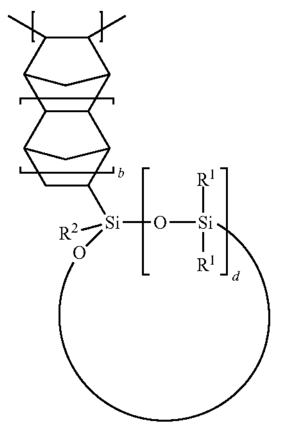

wherein $R^1$, $R^2$, and b are the same as described above, and d is an integer of 2 or more and 5 or less.

<7> The composition for external preparation for skin according to any one of the above <1> to <6>, wherein the component (A) is preferably a norbornane structure-containing silicone-modified polymer, more preferably a silicone-modified polynorbornene, even preferably a silicone-modified polynorbornene of the following formula (6):

(6)

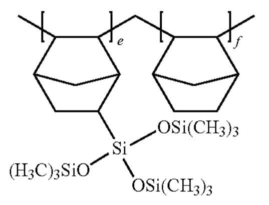

wherein e and f are the numbers of repeating units and each independently an integer of 1 or more.

<8> The composition for external preparation for skin according to the above <7>, wherein, in the formula (6), a ratio of e and f, e/f, is preferably from 20/80 to 90/10 (mol/mol), more preferably from 30/70 to 80/20 (mol/mol), even preferably from 50/50 to 70/30 (mol/mol).

<9> The composition for external preparation for skin according to any one of the above <1> to <8>, wherein the component (A) is preferably one or more selected from the group consisting of silicone-modified polynorbornenes, silicone-modified Pullulans, trimethylsiloxysilicic acid, trifluoropropyldimethyl/trimethylsiloxysilicic acid, and acrylic silicone dendrimers, more preferably one or more selected from the group consisting of silicone-modified polynorbornenes, silicone-modified Pullulans, trimethylsiloxysilicic acid, and trifluoropropyldimethyl/trimethylsiloxysilicic acid, even preferably one or more selected from the group consisting of silicone-modified polynorbornenes and silicone-modified Pullulans, even more preferably a silicone-modified polynorbornene.

<10> The composition for external preparation for skin according to any one of the above <1> to <9>, wherein a content of the component (A) is preferably 2 mass % or more, more preferably 4 mass % or more, even preferably 5 mass % or more, and preferably 25 mass % or less, more preferably 20 mass % or less, even preferably 18 mass % or less in the whole composition.

<11> The composition for external preparation for skin according to any one of the above <1> to <10>, wherein, in the component (B), the volatilization rate after drying at 1 atmosphere, 40° C., and R.H. of 60% for 30 minutes is preferably 18% or more, more preferably 25% or more, even preferably 30% or more, even more preferably 45% or more, even more preferably 65% or more, even more preferably 80% or more, even more preferably 95% or more.

<12> The composition for external preparation for skin according to any one of the above <1> to <11>, wherein the component (B) is preferably one or more selected from the group consisting of hydrocarbon oils and silicone oils, more preferably one or more selected from the group consisting of isododecane, hexamethyldisiloxane, methyl trimethicone, and polydimethylsiloxane having kinematic viscosity of 2 cSt or less at 25° C., even preferably one or more selected from the group consisting of isododecane, hexamethyldisiloxane, and polydimethylsiloxane having kinematic viscosity of 1.5 cSt or less at 25° C., even more preferably one or more selected from the group consisting of hexamethyldisiloxane and polydimethylsiloxane having kinematic viscosity of 1 cSt or less at 25° C., even more preferably hexamethyldisiloxane.

<13> The composition for external preparation for skin according to any one of the above <1> to <12>, wherein a content of the component (B) is preferably 1 mass % or more, more preferably 30 mass % or more, even preferably 50 mass % or more, even more preferably 70 mass % or more, even more preferably 75 mass % or more, and preferably 99 mass % or less, more preferably 98 mass % or less, even preferably 97 mass % or less, even more preferably 94 mass % or less, even more preferably 92 mass % or less, even more preferably 90 mass % or less in the whole composition.

<14> The composition for external preparation for skin according to any one of the above <1> to <13>, wherein a mass ratio of the component (A) to the component (B), (A)/(B), is preferably 0.02 or more, more preferably 0.03 or more, even preferably 0.04 or more, even more preferably 0.05 or more, even more preferably 0.1 or more, and preferably 1 or less, more preferably 0.7 or less, even preferably 0.4 or less, even more preferably 0.25 or less, even more preferably 0.24 or less.

<15> The composition for external preparation for skin according to any one of the above <1> to <14>, wherein a powder which is the component (C) comprises (C-1) an inorganic powder having a refractive index of from 1.3 to 1.8, preferably an inorganic powder having a refractive index of from 1.4 to 1.7, more preferably an inorganic powder having a refractive index of from 1.4 to 1.6.

<16> The composition for external preparation for skin according to any one of the above <1> to <15>, wherein the inorganic powder having a refractive index of from 1.3 to 1.8 which is the component (C-1) is preferably one or more selected from the group consisting of zeolite (refractive index, from 1.47 to 1.49), silica (refractive index, 1.54), talc (refractive index, from 1.54 to 1.59), sericite (refractive index, 1.58), mica (refractive index, 1.58), barium carbonate (refractive index, 1.6), barium sulfate (refractive index, 1.64), hydroxyapatite (refractive index, 1.65), calcium carbonate (refractive index, 1.66), and alumina (refractive index, 1.77), more preferably one or more selected from the group consisting of zeolite, silica, talc, sericite, mica, barium carbonate, barium sulfate, hydroxyapatite, and calcium carbonate, even more preferably one or more selected from the group consisting of silica, sericite, mica, and barium sulfate.

<17> The composition for external preparation for skin according to any one of the above <1> to <16>, wherein the inorganic powder having a refractive index of from 1.3 to 1.8 which is the component (C-1) is preferably a hydrophobization-treated inorganic powder, more preferably a silicone-treated inorganic powder.

<18> The composition for external preparation for skin according to any one of the above <1> to <17>, wherein a content of an inorganic powder which is the component (C-1) is preferably 1 mass % or more, more preferably 2 mass % or more, even more preferably 3 mass % or more, and preferably 15 mass % or less, more preferably 10 mass % or less, even more preferably 8 mass % or less in the whole composition.

<19> The composition for external preparation for skin according to any one of the above <1> to <18>, wherein a mass ratio of the component (A) to the component (C-1), (A)/(C-1), is preferably 1 or more and preferably 50 or less, more preferably 22 or less, even more preferably 10 or less, even more preferably 5 or less.

<20> The composition for external preparation for skin according to any one of the above <1> to <19>, wherein an average particle diameter of the component (C) is preferably 0.01 μm or more, more preferably 0.1 μm or more, even more preferably 1 μm or more, and preferably 100 μm or less, more preferably 30 μm or less, even more preferably 15 μm or less.

<21> The composition for external preparation for skin according to any one of the above <1> to <20>, wherein a content of the component (C) is preferably 0.1 mass % or more, more preferably 1 mass % or more, even more preferably 2 mass % or more, even more preferably 3 mass % or more, and preferably 40 mass % or less, more preferably 20 mass % or less, even more preferably 15 mass % or less, even more preferably 10 mass % or less in the whole composition.

<22> The composition for external preparation for skin according to any one of the above <1> to <21>, wherein the mass ratio of the component (A) to the component (C), (A)/(C), is preferably 1 or more and preferably 50 or less, more preferably 22 or less, even more preferably 10 or less, even more preferably 5 or less.

<23> A composition for external preparation for skin comprising the following components (A), (B), and (C):

(A) from 1 to 30 mass % of one or more selected from the group consisting of silicone-modified polynorbornenes and silicone-modified Pullulans, (B) from 1 to 99 mass % of a volatile oil having a volatilization rate of 14% or more after drying at 1 atmosphere, 40° C., and R.H. of 60% for 30 minutes, (C) from 0.1 to 40 mass % of a powder, wherein a mass ratio of the component (A) to the component (C), (A)/(C), is from 1 to 50, wherein from 0.1 to 30 mass % of at least (C-1) an inorganic powder having a refractive index of from 1.3 to 1.8 is comprised as the component (C) in the composition.

<24> A composition for external preparation for skin comprising the following components (A), (B), and (C):

(A) from 1 to 30 mass % of a silicone-modified polynorbornene, (B) from 1 to 99 mass % of a volatile oil having a volatilization rate of 14% or more after drying at 1 atmosphere, 40° C., and R.H. of 60% for 30 minutes, (C) from 0.1 to 40 mass % of a powder, wherein a mass ratio of the component (A) to the component (C), (A)/(C), is from 1 to 50, wherein from 0.1 to 30 mass % of at least (C-1) an inorganic powder having a refractive index of from 1.3 to 1.8 is comprised as the component (C) in the composition.

<25> A composition for external preparation for skin comprising the following components (A), (B), and (C):

(A) from 4 to 20 mass % of one or more selected from the group consisting of silicone-modified polynorbornenes and silicone-modified Pullulans, (B) from 50 to 94 mass % of a volatile oil having a volatilization rate of 14% or more after drying at 1 atmosphere, 40° C., and R.H. of 60% for 30 minutes, (C) from 2 to 15 mass % of a powder, wherein a mass ratio of the component (A) to the component (C), (A)/(C), is from 1 to 10, wherein from 2 to 10 mass % of at least (C-1) an inorganic powder having a refractive index of from 1.3 to 1.8 is comprised as the component (C) in the composition.

<26> A composition for external preparation for skin comprising the following components (A), (B), and (C):

(A) from 4 to 20 mass % of a silicone-modified polynorbornene, (B) from 50 to 94 mass % of a volatile oil having a volatilization rate of 14% or more after drying at 1 atmosphere, 40° C., and R.H. of 60% for 30 minutes, (C) from 2 to 15 mass % of a powder, wherein a mass ratio of the component (A) to the component (C), (A)/(C), is from 1 to 10, wherein from 2 to 10 mass % of at least (C-1) an inorganic powder having a refractive index of from 1.3 to 1.8 is comprised as the component (C) in the composition.

<27> The composition for external preparation for skin according to any one of the above <1> to <26>, which preferably further comprises a surfactant, more preferably a nonionic surfactant, even preferably a nonionic surfactant having HLB of 1 to 7.

<28> The composition for external preparation for skin according to the above <27>, wherein a content of the nonionic surfactant is preferably 30 mass % or less, more preferably 10 mass % or less, even preferably 5 mass % or less, even more preferably 3 mass % or less, even more preferably 1 mass % or less in the whole composition.

<29> The composition for external preparation for skin according to any one of the above <1> to <28>, wherein a content of water is preferably 50 mass % or less, more preferably 30 mass % or less, even preferably 10 mass % or less, even more preferably 5 mass % or less, even more preferably 1 mass % or less in the whole composition.

<30> Use of the composition for external preparation for skin according to any one of the above <1> to <29> as a skin wrinkle improving agent.

EXAMPLES

The present invention is described below with reference to examples, but the scope of the present invention is not limited to these examples. Of note, various measurements and assessments were performed by the following methods in the examples.

(Number Average Molecular Weight (Mn))

The number average molecular weight of a polymer was measured under the following conditions by gel filtration chromatography (GPC) using polystyrene as a reference substance.

Measuring device: HLC-8320GPC (manufactured by Tosoh Corporation)

Columns: K-806L (Shodex brand column manufactured by Showa Denko), two columns in series Detector: RI Eluent: 1 mmol/L-FARMIN DM20 (manufactured by Kao Corporation)/$CHCl_3$ Flow rate: 1.0 mL/min Column temperature: 40° C.

(Ratio of Deformation)

A 10 mass % hexamethyldisiloxane solution of a polymer which is the component (A) used for each composition was prepared. 0.005 g of this solution was applied to an area of 20 mm width×50 mm length (a portion of 2 shown in FIG. 1 (*a*)) on one side of a polyethylene sheet 1 of 20 mm width (W)×100 mm length (L0)×0.03 mm thickness ("LL film" manufactured by Enshu Chemical Industries Inc.) shown in FIG. 1 (*a*) in the length direction from one end 1*a* of a short side of the polyethylene sheet 1, and the polyethylene sheet was dried in a thermostatic oven set at 40° C. for 10 minutes. Assuming the length of the polyethylene sheet portion coated with the solution as L1 (50 mm) and the length of the polyethylene sheet portion deformed (curled) by shrinkage after drying as L2 in the polyethylene sheet after drying (FIG. 1 (*b*)), L2/L1 was calculated, and the value was defined as a ratio of deformation of the polymer. L2 was obtained as the mean of values measured on two long sides of the polyethylene sheet 1.

(Bend Resistance)

A 30 mass % hexamethyldisiloxane solution of a polymer which is the component (A) used for each composition was prepared. This solution was applied to a polyethylene terephthalate film ("Lumirror 100T60" manufactured by Toray Industries, Inc.) of 50 mm width×100 mm length×0.1 mm thickness using a 200 m applicator, and the polyethylene terephthalate film was dried in a thermostatic oven set at 40° C. for 120 minutes to prepare a polymer film-added film (test piece).

Using the obtained test piece, a bend resistance test was performed in accordance with a cylindrical mandrel method defined in JIS K5600-5-1:1999. A bend resistance test was performed with a type 1 bend tester (Bend Tester Model 266 manufactured by Erichsen Inc.) using cylindrical mandrels of 32 mm, 25 mm, 20 mm, 16 mm, 12 mm, 10 mm, 8 mm, 6 mm, 4 mm, 3 mm, and 2 mm in diameter sequentially, starting with a cylindrical mandrel of the longest diameter, while the polymer film side face of the test piece was allowed to face outside. The test was stopped at a time point when a crack occurred in the polymer film, and the minimum diameter of the cylindrical mandrel (mm) with which a crack did not occur was obtained as the value of bend resistance. A smaller value of this minimum diameter means better bend resistance.

(Volatilization Rate)

0.5 g of the sample was placed in a glass petri dish of 40 mm in diameter and left and dried on a hot plate set at 40° C. in an environment of 1 atmosphere and R.H. of 60% for 30 minutes. Assuming the sample mass before drying as $W_0$ (g) and the sample mass after drying as $W_1$ (g), the volatilization rate (%) was defined as a value of $\{(W_0-W_1)/W_0\}\times 100$. A larger value of this volatilization rate means a faster volatilization speed and easier drying.

(Wrinkle Improving Effect)

Figure 2:
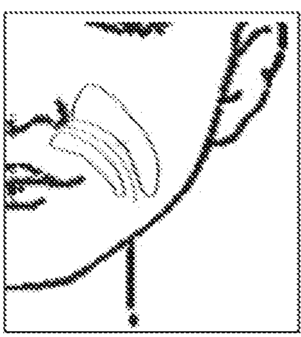
FIG. 2 shows how each composition for external preparation for skin is applied when a wrinkle improving effect thereof is assessed in the examples.

Five expert panelists applied 0.2 g of each composition with fingers to nasolabial folds around the mouth on a half side of the face while pinching them in a form shown in FIG. 2. After drying at room temperature (25° C.) for 10 minutes, sensory evaluation was performed with the following criteria to assess the wrinkle improving effect. The result was expressed as the sum of scores given by the five panelists.

5: Wrinkles have become considerably thinner.

4: Wrinkles have become thinner.

3: Wrinkles have become slightly thinner.

2: Wrinkles have remained and hardly changed.

1: Wrinkles are unchanged.

(Suppression of Shininess)

Five expert panelists applied each composition to the skin, and after drying, sensory evaluation was performed with the following criteria to assess shininess of the coating film on the skin. The result is expressed as the sum of scores given by the five panelists.

5: The coating film is not shiny.

4: The coating film is not very shiny.

3: Part of the coating film looks slightly shiny.

2: Part of the coating film looks shiny.

1: The whole coating film looks shiny.

(Finish (Uniform))

Five expert panelists applied each composition to the skin, and after drying, sensory evaluation was performed with the following criteria to assess uniformity of the finish. The result was expressed as the sum of scores given by the five panelists.

5: The finish looks considerably uniform.

4: The finish looks uniform.

3: The finish looks slightly uniform.

2: The finish looks slightly non-uniform.

1: The finish looks non-uniform.

(Less Noticeable Boundary Between the Coating Film and Bare Skin)

Five expert panelists applied each composition to the skin, and after drying, sensory evaluation was performed with the following criteria to assess the less noticeableness of the boundary between the coating film and bare skin on the skin. The result is expressed as the sum of scores given by the five panelists.

5: The boundary is not noticeable.

4: The boundary is not very noticeable.

3: The boundary is slightly noticeable.

2: The boundary is noticeable.

1: The boundary is clearly noticeable.

(Fine Finish)

Five expert panelists applied each cosmetic liquid to the skin, and after drying, sensory evaluation was performed with the following criteria to assess the finish on the skin. The result is expressed as the sum of scores given by the five panelists.

5: The finish is considerably fine.

4: The finish is fine.

3: The finish is slightly fine.

2: The finish is not very fine.

1: The finish is not fine.

Examples 1 to 12, Comparative Examples 1 to 2

Compositions for external preparation for skin (liquid) having the compositions shown in Table 1 were manufactured, and the wrinkle improving effect, suppression of shininess, finish (uniform), less noticeable boundary between the coating film and bare skin, and fine finish were assessed. The results are shown with the compositions in Table 1.

(Manufacturing Method)

An oil phase component obtained by mixing the components (A), (B), and (C) was dispersed with a disperser and stirred with a homo mixer to obtain compositions for external preparation for skin (liquid).

TABLE 1

| Component (mass %) | | Raw material | Examples 1 | 2 | 3 | 4 | 5 | 6 | 7 |
|---|---|---|---|---|---|---|---|---|---|
| Component (A) | (Norbornene-tris(trimethylsiloxy) silylnorbornene) copolymer solid content*[1] | manufactured by Shin-Etsu Chemical Co., Ltd. NBN-30-ID | 13.0 | 13.0 | 13.0 | 5.0 | 18.0 | 13.0 | 13.0 |
| | Silicone-modified Pullulan solid content*[2] | manufactured by Shin-Etsu Chemical Co., Ltd. TSPL-30-ID | | | | | | | |
| | Trimethyl-siloxysilicic acid solid content*[3] | manufactured by Shin-Etsu Chemical Co., Ltd. X-21-5595 | | | | | | | |
| Component (B) | Hexamethyl-disiloxane | manufactured by Shin-Etsu Chemical Co., Ltd. KF-96L-0.65cs | 53.7 | 51.7 | 48.7 | 78.3 | 35.0 | 51.7 | 51.7 |
| | Isododecane | Marukasol R manufactured by Maruzen Petrochemical Co., Ltd. | 30.3 | 30.3 | 30.3 | 11.7 | 42.0 | 30.3 | 30.3 |
| Component (C) | (C-1) Dimeticone-treated silica | SA-SB-300 manufactured by Miyoshi Kasei Inc. (refractive index, 1.54; average particle diameter, from 3 to 7 μm) | 3.0 | 5.0 | 8.0 | 5.0 | 5.0 | | |
| | (C-1) Sericite | Sericite FSE manufactured by Sanshin Mining Ind. Co., Ltd. (refractive index, 1.58; average particle diameter, 10 μm) | | | | | | 5.0 | |
| | (C-1) Mica | SA-310 manufactured by Yamaguchi Mica Co., Ltd. (refractive index, 1.58; average particle diameter, 26 μm) | | | | | | | 5.0 |
| | (C-1) Barium sulfate | Plate-like barium sulfate (H) (Sakai Chemical Industry Co., Ltd.; refractive index, 1.64; average particle diameter, 7 μm) | | | | | | | |
| | Titanium oxide | CR-50 (Ishihara Sangyo Kaisha, Ltd.; refractive index; average particle diameter, 0.25 μm) | | | | | | | |
| | Iron oxide (red iron oxide, yellow iron oxide, black iron oxide) | | | | | | | | |
| | Total | | 100.0 | 100.0 | 100.0 | 100.0 | 1000 | 100.0 | 100.0 |
| | (A) | | 13.0 | 13.0 | 13.0 | 5.0 | 18.0 | 13.0 | 13.0 |
| | (B) | | 84.0 | 82.0 | 79.0 | 90.0 | 77.0 | 82.0 | 82.0 |
| | (C) | | 3.0 | 5.0 | 8.0 | 5.0 | 5.0 | 5.0 | 5.0 |
| | (C-1) | | 3.0 | 5.0 | 8.0 | 5.0 | 5.0 | 5.0 | 5.0 |
| | (A)/(B) | | 0.15 | 0.16 | 0.16 | 0.06 | 0.23 | 0.16 | 0.16 |
| | (A)/(C) | | 4.3 | 2.6 | 1.6 | 1.0 | 3.6 | 2.6 | 2.6 |
| | (A)(C-1) | | 4.3 | 2.6 | 1.6 | 1.0 | 3.6 | 2.6 | 2.6 |
| Component (A) Polymer property | Ratio of deformation measured by method (1) | | 1.0 | 1.0 | 1.0 | 1.0 | 1.0 | 1.0 | 1.0 |
| | Bend resistance measured by method (2) (Minimum diameter of the cylindrical mandrel which causes no cracks in the polymer film: mm) | | 4 | 4 | 4 | 4 | 4 | 4 | 4 |
| | Ratio of deformation/minimum diameter of the mandrel | | 0.250 | 0.250 | 0.250 | 0.250 | 0.250 | 0.250 | 0.250 |
| Component (B) Property | Volatilization rate (%) | | 78.8 | 76.2 | 74.4 | 97.2 | 59.3 | 76.2 | 76.2 |
| Assessment | Wrinkle improving effect | | 25 | 25 | 25 | 20 | 25 | 25 | 25 |
| | Suppression of shininess | | 24 | 23 | 25 | 24 | 23 | 22 | 21 |
| | Finish (uniform) | | 22 | 25 | 23 | 24 | 21 | 23 | 23 |
| | Less noticeable boundary between the coating film and bare skin | | 24 | 25 | 23 | 24 | 21 | 22 | 20 |
| | Fine finish | | 23 | 24 | 22 | 23 | 20 | 23 | 20 |

TABLE 1-continued

| | | | Examples | | | | | Comparative Examples | |
|---|---|---|---|---|---|---|---|---|---|
| | | | 8 | 9 | 10 | 11 | 12 | 1 | 2 |
| Component (A) | (Norbornene-tris(trimethylsiloxy) silylnorbornene) copolymer solid content*1 | manufactured by Shin-Etsu Chemical Co., Ltd. NBN-30-ID | 13.0 | 13.0 | 13.0 | | | 13.0 | 10.0 |
| | Silicone-modified Pullulan solid content*2 | manufactured by Shin-Etsu Chemical Co., Ltd. TSPL-30-ID | | | | 13.0 | | | |
| | Trimethyl-siloxysilicic acid solid content*3 | manufactured by Shin-Etsu Chemical Co., Ltd. X-21-5595 | | | | | 13.0 | | |
| Component (B) | Hexamethyl-disiloxane | manufactured by Shin-Etsu Chemical Co., Ltd. KF-96L-0.65cs | 51.7 | 51.6 | 50.6 | 51.7 | 51.7 | 56.7 | 53.7 |
| | Isododecane | Marukasol R manufactured by Maruzen Petrochemical Co., Ltd. | 30.3 | 30.3 | 30.3 | 30.3 | 30.3 | 30.3 | 23.3 |
| Component (C) | (C-1) Dimeticone-treated silica | SA-SB-300 manufactured by Miyoshi Kasei Inc. (refractive index, 1.54; average particle diameter, from 3 to 7 μm) | | 5.0 | 5.0 | 5.0 | 5.0 | | 13.0 |
| | (C-1) Sericite | Sericite FSE manufactured by Sanshin Mining Ind. Co., Ltd. (refractive index, 1.58; average particle diameter, 10 μm) | | | | | | | |
| | (C-1) Mica | SA-310 manufactured by Yamaguchi Mica Co., Ltd. (refractive index, 1.58; average particle diameter, 26 μm) | | | | | | | |
| | (C-1) Barium sulfate | Plate-like barium sulfate (H) (Sakai Chemical Industry Co., Ltd.; refractive index, 1.64; average particle diameter, 7 μm) | 5.0 | | | | | | |
| | Titanium oxide | CR-50 (Ishihara Sangyo Kaisha, Ltd.; refractive index; average particle diameter, 0.25 μm) | | 0.1 | 1.0 | | | | |
| | Iron oxide (red iron oxide, yellow iron oxide, black iron oxide) | | | | 0.1 | | | | |
| | Total | | 100.0 | 100.0 | 100.0 | 100.0 | 100.0 | 100.0 | 1000 |
| | (A) | | 13.0 | 13.0 | 13.0 | 13.0 | 13.0 | 13.0 | 10.0 |
| | (B) | | 82.0 | 81.9 | 80.9 | 82.0 | 82.0 | 87.0 | 77.0 |
| | (C) | | 5.0 | 5.1 | 6.1 | 5.0 | 5.0 | — | 13.0 |
| | (C-1) | | 5.0 | 5.0 | 5.0 | 5.0 | 5.0 | 0.0 | 13.0 |
| | (A)/(B) | | 0.16 | 0.16 | 0.16 | 0.16 | 0.16 | 0.15 | 0.13 |
| | (A)/(C) | | 2.6 | 2.5 | 2.1 | 2.6 | 2.6 | — | 0.8 |
| | (A)(C-1) | | 2.6 | 2.6 | 2.6 | 2.6 | 2.6 | — | 0.8 |
| Component (A) Polymer property | Ratio of deformation measured by method (1) | | 1.0 | 1.0 | 1.0 | 0.9 | 0.8 | 1.0 | 1.0 |
| | Bend resistance measured by method (2) (Minimum diameter of the cylindrical mandrel which causes no cracks in the polymer film: mm) | | 4 | 4 | 4 | 8 | 25 | 4 | 4 |
| | Ratio of deformation/minimum diameter of the mandrel | | 0.250 | 0.250 | 0.250 | 0.113 | 0.032 | 0.250 | 0.250 |
| Component (B) Property | Volatilization rate (%) | | 76.2 | 82.9 | 82.4 | 76.2 | 76.2 | 81.5 | 84.4 |
| Assessment | Wrinkle improving effect | | 25 | 25 | 25 | 17 | 15 | 25 | 23 |
| | Suppression of shininess | | 22 | 22 | 22 | 20 | 20 | 6 | 25 |
| | Finish (uniform) | | 23 | 22 | 22 | 18 | 17 | 6 | 5 |
| | Less noticeable boundary between the coating film and bare skin | | 23 | 20 | 22 | 18 | 17 | 5 | 8 |
| | Fine finish | | 22 | 21 | 22 | 20 | 19 | 6 | 6 |

*1 to *3 in Table 1 are as follows:

*1: "NBN-30-ID" (an isododecane solution of a norbornene/tris(trimethylsiloxy)silylnorbornene copolymer with e/f of 60/40 (mol/mol) in the following formula (6) and Mn of 360,000; effective concentration: 30 mass %) manufactured by Shin-Etsu Chemical Co., Ltd. was dried under reduced pressure at 50° C. for 12 hours, and the obtained solid content was used.

(6)

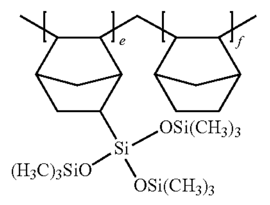

*2: "TSPL-30-ID" (an isododecane solution of tri(trimethylsiloxy)silyl propyl carbamide acid Pullulan; effective concentration: 30 mass %) manufactured by Shin-Etsu Chemical Co., Ltd. was dried under reduced pressure at 50° C. for 12 hours, and the obtained solid content was used.

*3: "X21-5595" (an isododecane solution of trimethylsiloxysilicic acid; effective concentration: 60 mass %) manufactured by Shin-Etsu Chemical Co., Ltd. was dried under reduced pressure at 50° C. for 12 hours, and the obtained solid content was used.

Examples 13 to 16

As in Examples 1 to 12, compositions for external preparation for skin having the compositions shown in Table 2 were manufactured.

All the obtained compositions for external preparation for skin can improve wrinkles and suppress shininess, achieve a fine, uniform finish, and make the boundary between the coating film and bare skin less noticeable.

TABLE 2

| Component (mass %) | | Raw material | Examples | | | |
|---|---|---|---|---|---|---|
| | | | 13 | 14 | 15 | 16 |
| Component (A) | (Norbornene/tris (trimethylsiloxy) silylnorbornene) copolymer solid content*1 | manufactured by Shin-Etsu Chemical Co., Ltd NBN-30-ID | 13.0 | | 12.5 | 12.5 |
| | Trifluoroalkyl-dimethyl trimethyl-siloxysilicic acid solid content*4 | manufactured by Momentive Performance Materials Japan LLC XS66-B8226 | | 13.0 | | |
| Component (B) | Hexamethyl-disiloxane | manufactured by Shin-Etsu Chemical Co., Ltd KF-96L-0.65cs | 36.7 | 51.7 | 36.7 | 36.7 |
| | Octamethyl-trisiloxane | manufactured by Shin-Etsu Chemical Co., Ltd KF-96L-1cs | 15.0 | | 15.0 | 15.0 |
| | Isododecane | Marukasol R manufactured by Maruzen Petro-chemical Co., Ltd. | 30.3 | 30.3 | 30.3 | 30.3 |
| Component (C) | (C-1) Dimeticone-treated silica | SA-SB-300 manufactured by Miyoshi Kasei Inc. (refractive index, 1.54; average particle diameter, from 3 to 7 μm) | 5.0 | 5.0 | 5.0 | |
| | (C-1) Silica | SB-300 manufactured by Miyoshi Kasei Inc. (refractive index, 1.54; average particle diameter, from 3 to 7 μm) | | | | 5.1 |
| Other components | Polyether-modified silicone | manufactured by Dow Corning Toray Co., Ltd. SH3775M | | | 0.3 | 0.2 |
| | Water | | | | 0.2 | 0.2 |
| | | | 100.0 | 100.0 | 100.0 | 100.0 |
| | (A) | | 13.0 | 13.0 | 12.5 | 12.5 |
| | (B) | | 82.0 | 82.0 | 82.0 | 82.0 |
| | (C) | | 5.0 | 5.0 | 5.0 | 5.1 |
| | (C-1) | | 5.0 | 5.0 | 5.0 | 5.1 |
| | (A)/(B) | | 0.16 | 0.16 | 0.15 | 0.15 |
| | (A)/(C) | | 2.6 | 2.6 | 2.5 | 2.5 |
| | (A)/(C-1) | | 2.6 | 2.6 | 2.5 | 2.5 |

TABLE 2-continued

| Component (mass %) | Raw material | Examples 13 | 14 | 15 | 16 |
|---|---|---|---|---|---|
| Component (A) Polymer property | Ratio of deformation measured by method (1) | 1.0 | 0.7 | 1.0 | 1.0 |
| | Bend resistance measured by method (2) (Minimum diameter of the cylindrical mandrel which causes no cracks in the polymer film: mm) | 4 | 25 | 4 | 4 |
| | Ratio of deformation/minimum diameter of the mandrel | 0.250 | 0.028 | 0.250 | 0.250 |
| Component (B) Property | Volatilization rate (%) | 46.3 | 76.2 | 46.3 | 46.3 |

*4 in Table 2 is as follows.

*4: "XS66-B8226" (a cyclopentasiloxane solution of trifluoropropyldimethyl/trimethylsiloxysilicic acid; effective concentration, 50 mass %) manufactured by Momentive Performance Materials Japan LLC was dried under reduced pressure at 50° C. for 12 hours, and the obtained solid was used.

REFERENCE SIGN LIST

1 A polyethylene sheet

1*a* One end of a short side of the polyethylene sheet 1

2 A portion coated with a polymer solution

The invention claimed is:

1. A composition for external preparation for skin comprising the following components (A), (B), and (C):

(A) a norbornene/tris(trimethylsiloxy)silylnorbornene copolymer, (B) a mixture comprising isododecane and hexamethyldisiloxane, and (C) a powder comprising (C-1) an inorganic powder having a refractive index of from 1.3 to 1.8, wherein a mass ratio of the component (A) to the component (C), (A)/(C), is from 1 to 50, wherein a content of the component (C-1) is from 0.1 to 30 mass % relative to a total mass of the composition, wherein a content of the component (A) is from 1 to 20 mass % and a content of the component (B) is from 30 to 98 mass %, each based on a total mass of the composition, and wherein a mass ratio of the component (A) to the component (B), (A)/(B), is from 0.02 to 0.4.

2. The composition for external preparation for skin according to claim 1, wherein the component (C-1) is one or more inorganic powders selected from the group consisting of zeolite, silica, talc, sericite, mica, barium carbonate, barium sulfate, hydroxyapatite, and calcium carbonate.

3. The composition for external preparation for skin according to claim 1, wherein a content of the component (C) is from 0.1 to 40 mass %.

4. The composition for external preparation for skin according to claim 1, wherein a mass ratio of the component (A) to the component (C-1), (A)/(C-1), is from 1 to 50.

* * * * *